United States Patent [19]

Nagy et al.

[11] Patent Number: 4,684,638

[45] Date of Patent: Aug. 4, 1987

[54] METAL COMPLEXES OF BIS-INDOLE COMPOUNDS AND AQUEOUS PHARMACEUTICAL COMPOSITIONS CONTAINING THEM

[75] Inventors: Géza Takács: Nagy; Gábor Szepesi; Maria Gazdag; Zsófia Papp née Sziklay; Kalmán Burger, all of Budapest, Hungary

[73] Assignee: Richter Gedeon Vegyeszeti Gyar Rt., Budapest, Hungary

[21] Appl. No.: 782,492

[22] Filed: Oct. 1, 1985

[30] Foreign Application Priority Data

Oct. 16, 1984 [HU] Hungary ................................. 3861

[51] Int. Cl.$^4$ .................. A61K 31/475; C07D 519/04
[52] U.S. Cl. .................................. 514/185; 514/283; 540/465; 540/478
[58] Field of Search ................ 540/478, 465; 514/185, 514/283

[56] References Cited

U.S. PATENT DOCUMENTS

| | | | |
|---|---|---|---|
| 2,008,252 | 7/1935 | Jostes et al. | 514/185 X |
| 3,426,024 | 2/1969 | Harvey | 546/10 X |
| 4,073,901 | 2/1978 | Buchel et al. | 548/109 X |
| 4,309,415 | 1/1982 | Horrobin | 514/283 |

OTHER PUBLICATIONS

Campean, et al., Chemical Abstracts, vol. 95, 35487c (1981), and Chemical Abstracts Chemical Subject Index, vol. 95, p. 7315CS.

*Primary Examiner*—Nicholas S. Rizzo
*Assistant Examiner*—Diana G. Rivers
*Attorney, Agent, or Firm*—Karl F. Ross; Herbert Dubno; Jonathan Myers

[57] ABSTRACT

The invention relates to new aqueous pharmaceutical compositions containing as active ingredient a pharmaceutically acceptable complex of a bis-indole compound with a bi- or multivalent metal ion in a therapeutically effective amount. The invention further relates to complexes formed between a bis-indole compound and a bi- or multivalent metal ion.

According to another aspect of the invention there is provided a process for the preparation of a pharmaceutically acceptable metal complex of a bis-indole compound and optionally stable aqueous pharmaceutical compositions containing said metal complex, in which a solution of a bis-indole compound or a pharmaceutically acceptable salt thereof in an aqueous medium is reacted with a non-toxic water soluble salt of a bi- or multivalent metal capable of complexation, at a pH of 3.0 to 6.0, optionally in the presence of or followed by the addition of a conventional pharmaceutical carrier and/or further additive, or, if desired, the obtained complex is isolated.

The aqueous pharmaceutical compositions according to the invention have substantially increased stability.

9 Claims, 5 Drawing Figures

METAL COMPLEXES OF BIS-INDOLE COMPOUNDS AND AQUEOUS PHARMACEUTICAL COMPOSITIONS CONTAINING THEM

FIELD OF THE INVENTION

The invention relates to new pharmaceutical compositions containing a compound with a bis-indole skeleton or a pharmaceutically acceptable salt thereof in a form stable in an aqueous medium. More particularly, the invention relates to pharmaceutical compositions containing a bis-indole compound in the form of its metal complex, said complex having increased stability in an aqueous medium compared to the stability of compositions containing the bis-indole compound alone. The invention also provides a process for the preparation of said compositions. The invention further relates to the new pharmaceutically acceptable metal complexes of bis-indole compounds as well as to a process for the preparation thereof.

BACKGROUND OF THE INVENTION

The first known compounds with a bis-indole skeleton were alkaloids occuring in the Vinca rosea L plant, from which first vinblastine (VLB) (see U.S. Pat. No. 3,097,137) and then vincristine (VCR) and leurosine (Leu; see U.S. Pat. Nos. 3,205,220 and 3,370,570) were isolated. Since some of these alkaloids showed excellent anti-tumor activity, several synthetically modified derivatives were prepared.

The known indole-dihydroindole compounds successfully applied in tumor therapy are shown in formula (I)

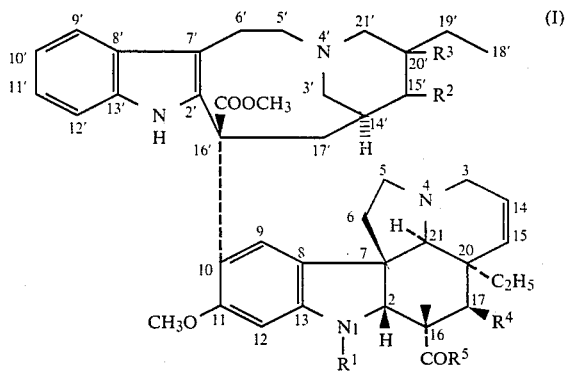

Formula (I) covers two groups of known anti-tumor agents, in one group $R^1$ stands for a methyl, and in the other one $R^1$ stands for a formyl group.

Thus, in the first case the meaning of the substituents is as follows:
$R^1$ represents a methyl group,
$R^2$ is hydrogen,
$R^3$ is a hydroxyl group, or
$R^2$ and $R^3$ form together a valence bond,
$R^4$ is a hydroxyl or an acetoxy group, and
$R^5$ stands for a methoxy or an amino group.

In the other case the definition of the substituents is as follows:
$R^1$ represents a formyl group,
$R^2$ is hydrogen and
$R^3$ is hydroxyl, or
$R^2$ and $R^3$ form together an epoxy group,
$R^4$ represents hydrogen or an acetoxy group and
$R^5$ is methoxy.

Preferred compounds covered by formula (I), wherein
$R^1$ stands for a methyl group are as follows: vinblastine (VLB), corresponding to formula (I), when
$R^2$ is hydrogen,
$R^3$ is hydroxyl,
$R^4$ is acetoxy,
$R^5$ is methoxy, and in the position 20' of the skeleton the hydroxy has $\beta$-, and the ethyl group has $\alpha$-configuration;
leurosidine, corresponding to formula (I), when
$R^2$, $R^3$, $R^4$ and $R^5$ have the same meaning as in the case of VLB, but in the position 20' of the skeleton the hydroxyl has $\alpha$-, and the ethyl group has $\beta$-configuration;
15',20'-anhydro-vinblastine, corresponding to formula (I), when
$R^2$ and $R^3$ form together a valence bond,
$R^4$ is acetoxy, and
$R^5$ is a methoxy group; and
vindesine, corresponding to formula (I), when
$R^2$ is hydrogen,
$R^3$ is hydroxyl,
$R^4$ is hydroxyl, and
$R^5$ is an amino group, and in the position 20' the hydroxyl has $\beta$-, and the ethyl group has $\alpha$-configuration.

Preferred compounds covered by formula (I), wherein
$R^1$ represents a formyl group, are as follows: vincristine (VCR), corresponding to formula (I), when
$R^2$ is hydrogen,
$R^3$ is hydroxyl,
$R^4$ is acetoxy, and
$R^5$ is a methoxy group, and in position 20' the hydroxy has $\beta$- and the ethyl group has $\alpha$-configuration;
N-desmethyl-N-formyl-leurosine, corresponding to formula (I), when
$R^2$ and $R^3$ form together an $\alpha$—$\alpha$ epoxy bridge,
$R^4$ is acetoxy and
$R^5$ is a methoxy group, and the ethyl group in the position 20' has $\beta$-configuration;
17-desacetoxy-vincristine, corresponding to formula (I), when
$R^4$ is a hydrogen, and the other substituents are the same as in the case of VCR; and
15',20'-anhydro-vincristine, corresponding to formula (I), when
$R^2$ and $R^3$ form together a valence bond,
$R^4$ is acetoxy and
$R^5$ is a methoxy group.

Bis-indole compounds are generally administered intravenously to patients suffering from neoplastic disease. For this purpose the active compounds should be brought into a stable solution form (i.e. injectable solution or infusion) which is directly injectable to the patients. However, in consequence of the insufficient stability of the dimer-indole compounds in gaseous solutions, until quite recently there was slight hope of having a directly utilizable formulation. The three bis-indole compounds, i.e. the vincristine, vinblastine and vindesine customarily used in clinical practice were available in two separate ampoules, one containing the lyophilized active ingredient (power ampoule) and the other one containing the sterile solvent (solvent ampoule) to dissolve the active component before use. This two-ampoule package, however, has several drawbacks. Firstly, the lyophilization is expensive, secondly the dissolution of each lyophilized sample should be carried out according to approved sterility and pyrogen-free standards to avoid risks in administration.

An improved process for the formulation of vinca dimers is disclosed in Belgian patent specification No. 897,280. According to said process, aqueous medical compositions containing a vinca dimer are prepared by dissolving a pharmaceutically acceptable salt of a vinca dimer and adding to the solution a polyol, and acetate buffer to maintain the pH of the solution at a value from 3 to 5, and a bacteriostatic agent. There are no storage-stability tests described, it is simply stated that 94–99% of the original active ingredient content are present after a 9-month storage period if the samples are stored at 5° C. In the meantime a one-ampoule vincristine composition was put on the market for which at 5° C. storage temperature a one year storage stability was guaranteed.

OBJECT OF THE INVENTION

Our aim was to provide a formulation for dimer indole compounds superior to the known ones, i.e. which is storage-stable even at room temperature for a long time.

DESCRIPTION OF THE DRAWING

It has been found that the bis-indole compounds and the acid addition salts thereof, respectively, readily form metal complexes with bi- or multivalent metal ions capable of complex formation, and the complexes obtained exhibit excellent stability properties in aqueous medium at a pH ranging from 3.0 to 6.0.

According to the present invention there is provided a process for the preparation of a pharmaceutically acceptable metal complex of a bis-indole compound and optionally stable aqueous pharmaceutical compositions containing said metal complex, in which a solution of a bis-indole compound or a pharmaceutically acceptable salt thereof in an aqueous medium is reacted with a non-toxic water soluble salt of a bi- or multivalent metal capable of complexation at a pH of 3.0 to 6.0 optionally in the presence of or followed by the addition of a conventional pharmaceutical carrier and/or further additive, or, if desired, the obtained metal complex is isolated.

Figure 1:
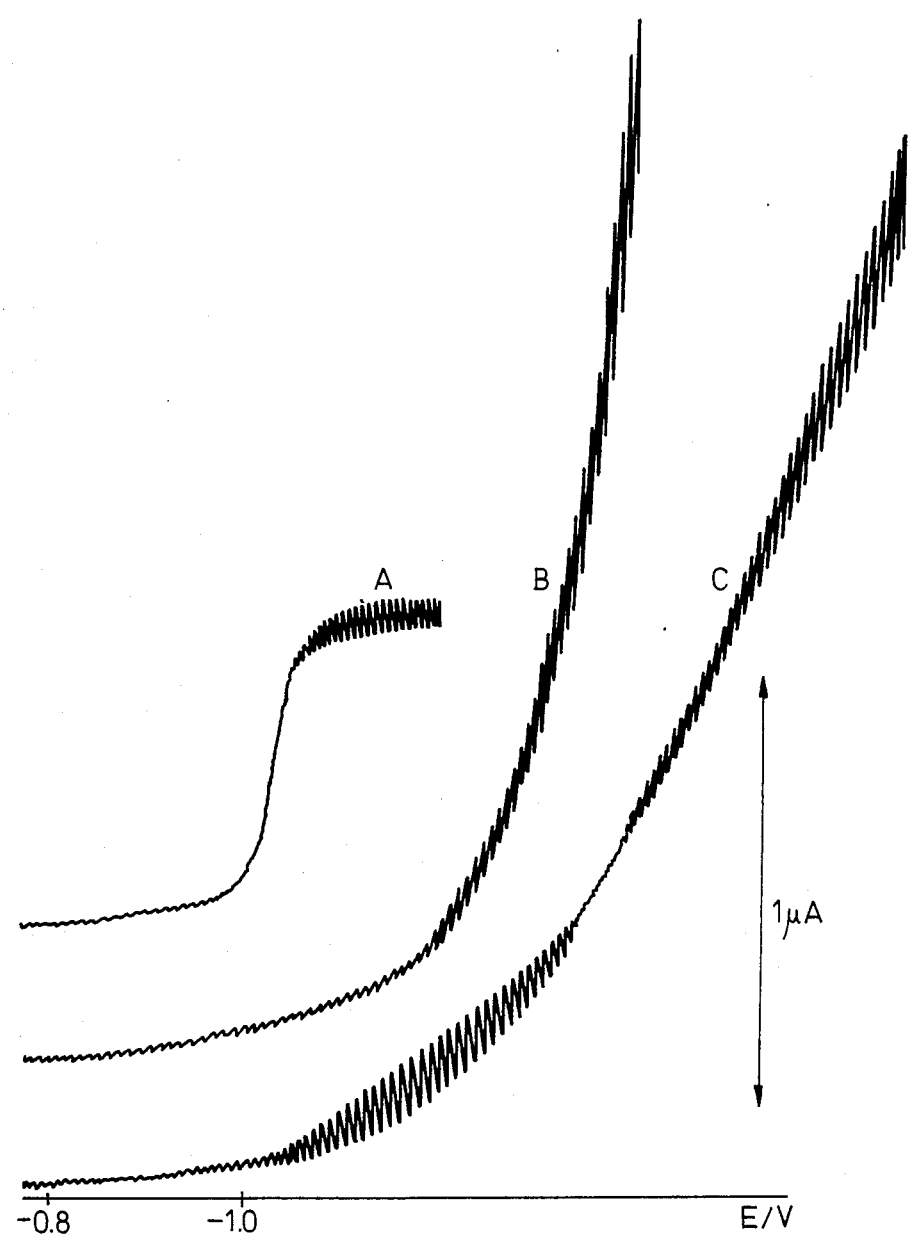

The novel complexes as well as the new formulations are also within the scope of the invention.

Two types of complexes formed by bis-indole alkaloids have been described so far. In C.A. 99:140214s (1983) N-2'-borane complex of 20'-deoxy-vinblastine was reported along with the structural analysis thereof. Tubuline complex of the vinblastine type alkaloids being more active than the free alkaloids are disclosed in Belgian patent specification No. 854,053. Tubuline, a protein of high molecular weight, forms a complex with vinblastine and the like at a pH value of 6.6 to 7.6 according to the disclosure. However, there is no mention as to the stability of any of the known complexes in aqueous solutions.

According to the present invention complex formation takes place between a bis-indole compound or a salt thereof and a water-soluble salt of a bi- or multivalent metal capable of complexation. Complexation is accomplished in water at a pH of 3 to 6.

Metal ions considered suitable for forming pharmaceutically acceptable complexes are e.g. zinc(II), magnesium(II), calcium(II), cobalt(II), iron(II) or nickel(II) ions. They are applicable in the form of their salts formed e.g. with saturated monobasic carboxylate anions, examples of which are formiate and acetate; or with an oxy-carboxylate anion having 6 carbon atoms, examples of which are gluconate, levulinate, lactobionate; with a disaccharide such as sucrose and with inorganic anions, such as sulphate or chloride. The most preferred metal ions are zinc(II), magnesium(II) and calcium(II) preferably when applied in the form of a gluconate or acetate salt.

The pH value ranging from 3.0 to 6.0 can be adjusted with a suitable buffer, preferably with an acetate buffer being a mixture of sodium acetate and acetic acid, which maintains the required pH value in the course of the complexation.

When solutions ready-to-use for injection purposes are to be prepared, the bis-indole compound is used as a pharmaceutically acceptable salt, in a therapeutically effective concentration. This concentration varies from one active ingredient to the next depending on the effective dose and therapeutic width of the individual bis-indole compounds. Generally 0.01 to 10 mg./ml., preferably 0.1 to 10 mg./ml., most preferably 0.5 to 1.0 mg./ml. concentration should be applied. One group of the bis-indole compounds covered by the formula (I), wherein $R^1$ stands for a formyl group, e.g. the vincristine or the like, is effective in a lower dosage range than the other group of compounds falling under the formula (I), wherein $R^1$ stands for a methyl group, e.g. the vinblastine and the like. Thus, vincristine type compounds generally should be applied at a lower concentration level than the vinblastine type alkaloids.

Equilibrium analysis of the systems showed that under the above conditions the bis-indole component and the metal ions are present in the complex predominantly in a 1:1 molar ratio. On the basis of the complex formation constant the metal component should be applied in a slight molar excess compared to the bis-indole compound to avoid incomplete complexation. Thus, for example to 1 mg. of vincristine sulphate 41 to 100 μg $Ca^{2+}$, preferably 50 μg calcium ion, or 24–55 μg $Mg^{2+}$, preferably 26–28 μg magnesium ion, or 66 to 140 μg $Zn^{2+}$, preferably 70 μg zinc ion should be added.

Injection solutions are isotonized with a hexose or a hexitol, examples of which are the glucose, mannitol and maltose. The actual quantity of the isotonizing agent can be determined by osmometry.

The solution may contain an auxiliary solvent such as ethanol or a glycol ether(polyalkyleneglycol) of higher molecular weight. In the composition the preferred quantities of the ethanol and glycol ether are 4–8% and 5–15%, respectively.

The stable, ready-to-use injection solutions may also contain a preservative generally used for this purpose, such as benzyl alcohol, Nipagin A, Nipagin M, nipasol (propylparaben) or a mixture thereof (nipacombine) in a concentration convenient to use.

As antioxidant e.g. sodium or potassium pyrosulphite can be used in 0.02–0.15%, preferably 0.05% concentration.

The pH of the stable solutions should be adjusted to a pH value ranging from 3.0 to 6.0, preferably to 3.5 to 5.0. In the case of vincristine the preferred pH value is 4.5 as approved by USP XX. In the presence of the employed metal salts a desired pH value is easy to maintain.

According to a preferred embodiment of the invention a sufficient amount of the metal salt used for complexation is dissolved in sterile distilled pyrogen-free water, optionally together with the additives convenient to use, such as an isotonizing agent, an auxiliary solvent, a buffer, a preservative and an antioxidant, and to the solution so obtained the aqueous solution of the desired bis-indole compound is added. The solution is made up to the final volume with bacteriostatic water for injection, is homogenized, subjected to sterile filtration and is distributed into sterile vials under inert gas atmosphere.

BRIEF DESCRIPTION OF THE DRAWING

Figure 2:
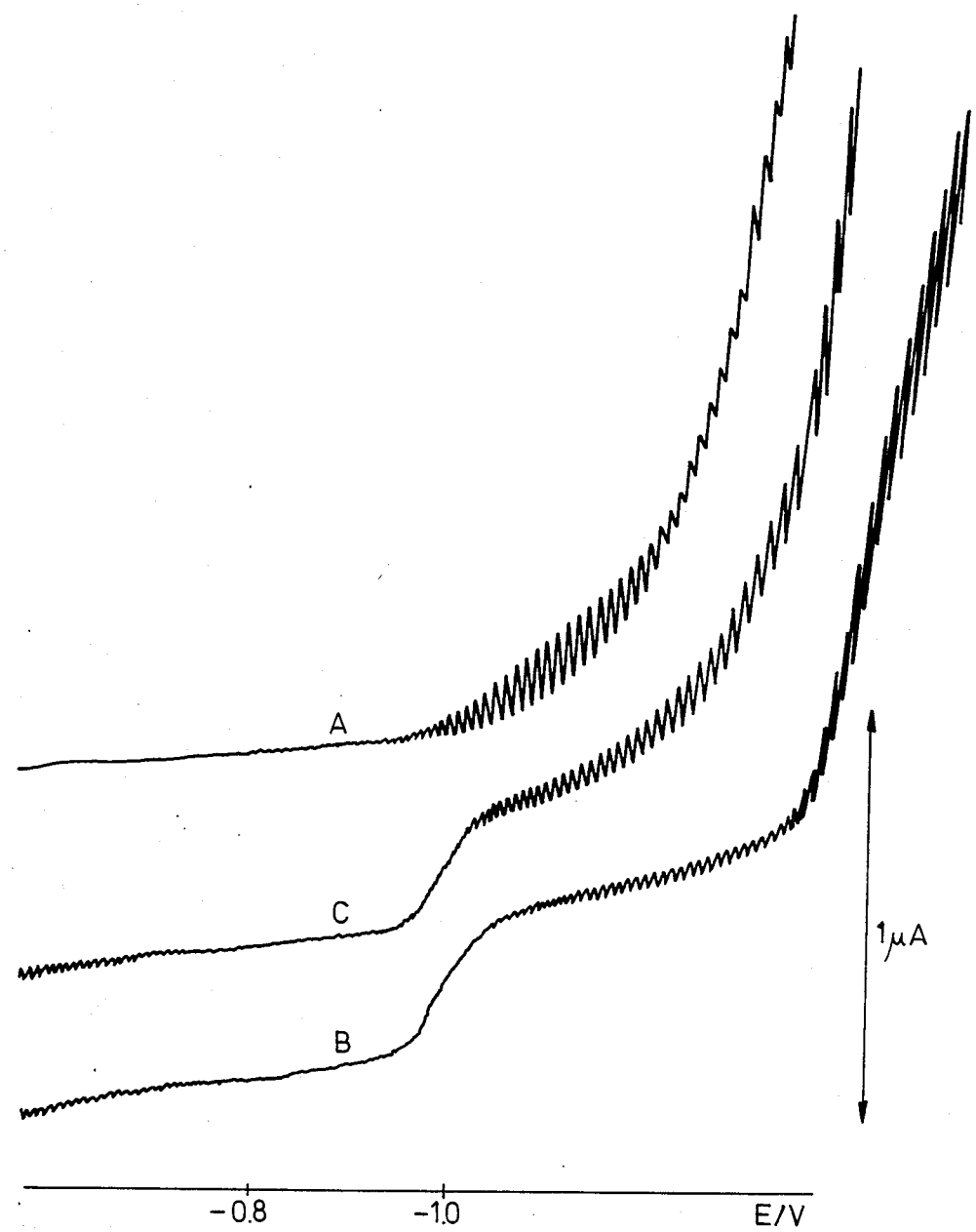
Figure 3:
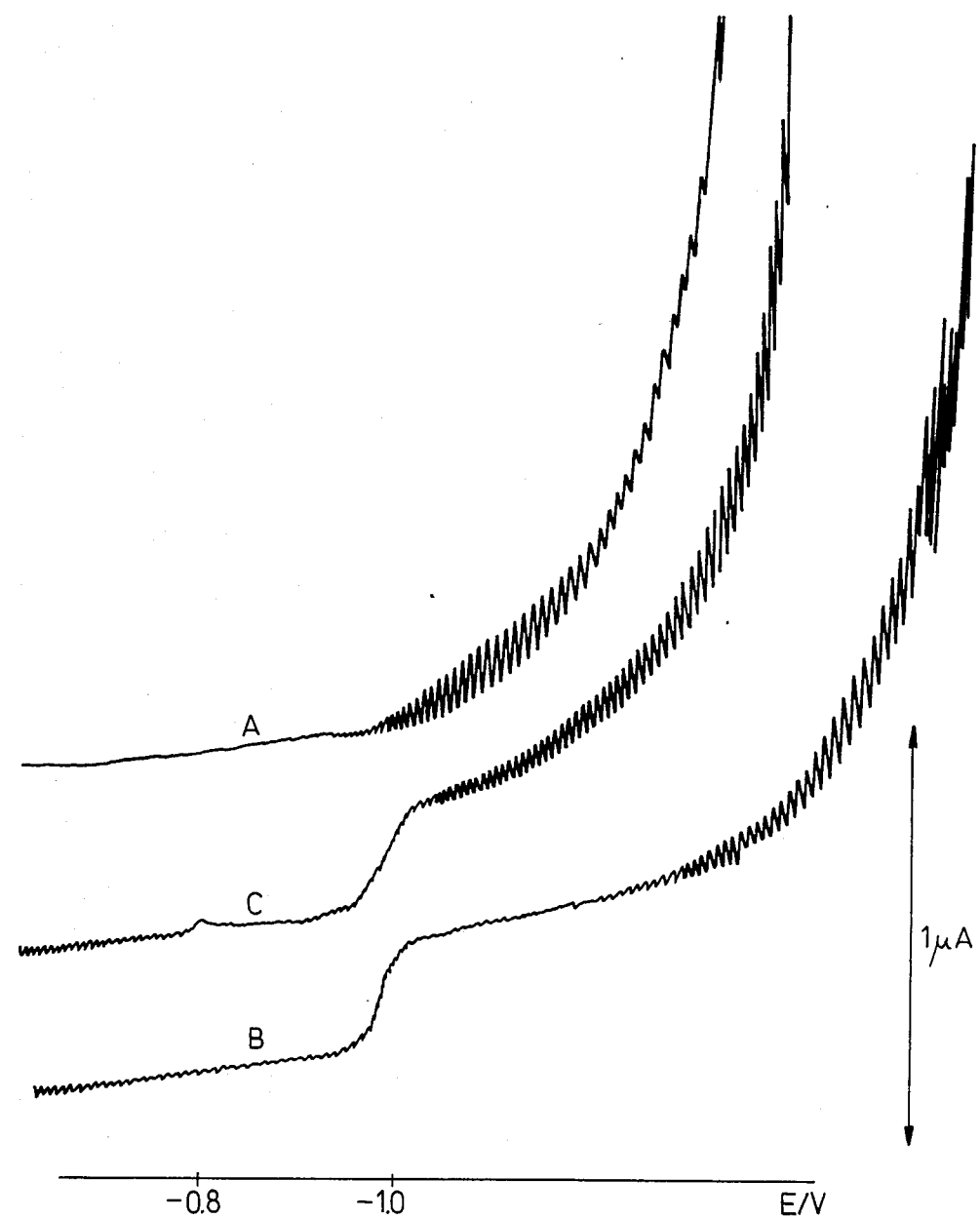

FIGS. 1-3 are polarograms illustrating techniques used; and

Figure 4:
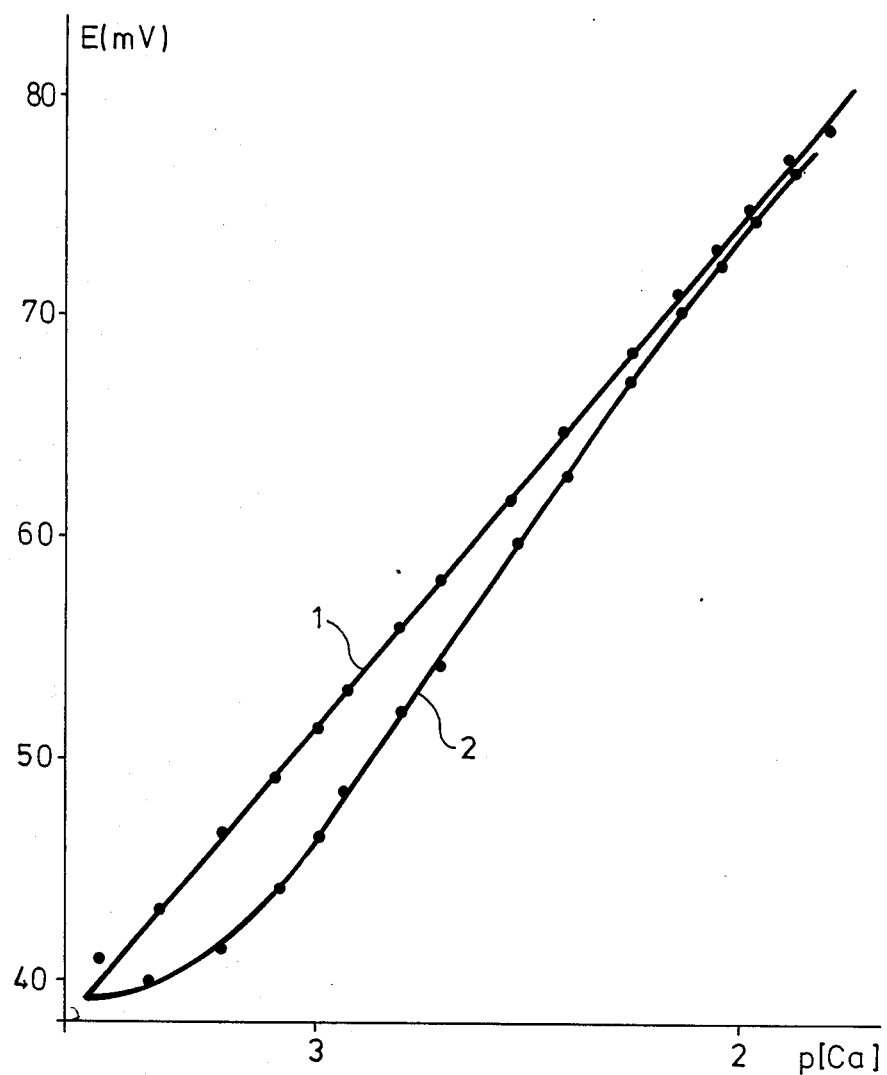
Figure 5:
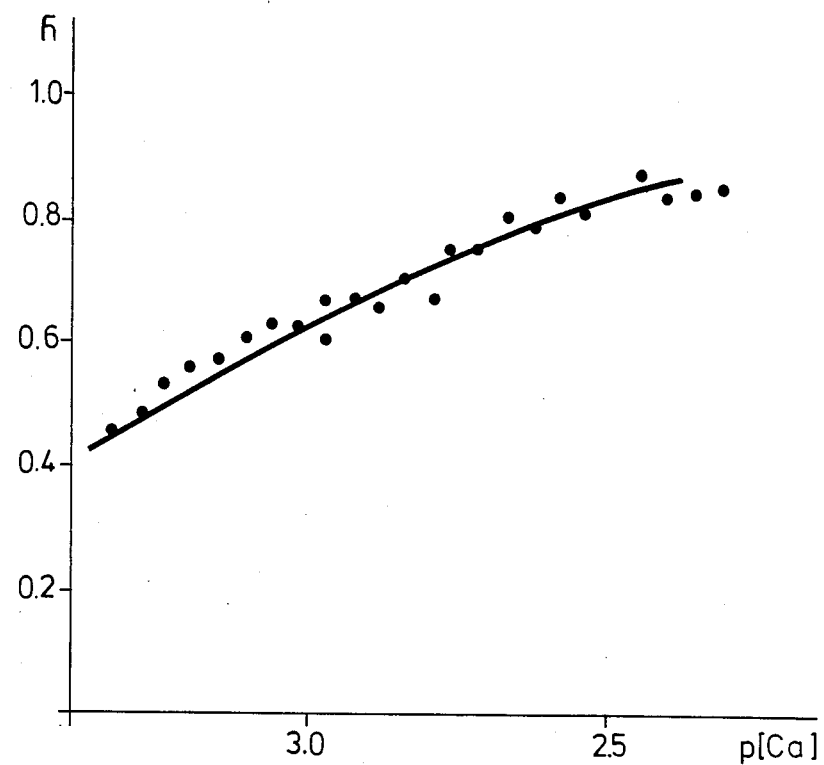

FIGS. 4 and 5 are graphs of results obtained.

SPECIFIC DESCRIPTION

The interaction between vincristine and certain metal ions, such as zinc, calcium and magnesium was studied by polarographic and potentiometric equilibrium measurements.

To investigate the VCR-zinc interaction a series of samples, each containing a constant amount of zinc ions ($10^{-4}$ mole/dm$^3$) and varying amounts of vincristine in the form of its sulphate salt ranging from $10^{-3}$ to $10^{-5}$ mole VCR/dm$^3$, were prepared. The pH of these aqueous solutions was adjusted to 5.5 with an acetic acid—sodium acetate buffer of 0.15 mole/dm$^3$ concentration (furtheron mentioned as buffer solution).

The samples were subjected to polarographic analysis. Three characteristic polarograms are shown in FIG. 1.

Polarogram A was obtained from the buffer solution containing $10^{-4}$ mole zinc chloride/dm$^3$.

Polarogram B was obtained from the buffer solution containing $10^{-4}$ mole zinc chloride/dm$^3$ and $5 \times 10^{-4}$ mole VCR/dm$^3$.

Polarogram C was obtained from the buffer solution containing both the zinc chloride and the VCR in $10^{-4}$ mole/dm$^3$ concentration.

The curves were interpreted as follows: when excess VCR is present, no zinc wave appears in the polarogram. This indicates the formation of a zinc complex of high stability. Oscillation indicating the initial appearance of the polarographic zinc wave was recorded at approximately 1:1 VCR:zinc molar ratio, just before the depolarization caused by the catalytic hydrogen wave. Further decrease in the VCR concentration resulted in the development of the zinc wave and when the VCR concentration was lowered to $2.5 \times 10^{-5}$ mole/dm$^3$ or below this value, the shape and half-wave potential of the wave did not show further changes and was the same as in the case of the free zinc ions.

The above results confirm that a stable complex was formed between zinc ions and VCR even at their 1:1 molar ratio.

Interaction between VCR and calcium or magnesium ions was studied indirectly, namely the effect of said metal ions on the polarographic properties of the VCR-zinc system was investigated. More particularly, to a solution containing VCR and zinc ions in 1:1 molar ratio (the signal indicating the presence of zinc just appears in the polarogram) gradually increasing amounts of calcium or magnesium chloride were added.

The effect of calcium ions is shown in FIG. 2, wherein Polarogram A was obtained from the buffer solution containing $10^{-4}$ mole/dm$^3$ zinc chloride and $10^{-4}$ mole/dm$^3$ VCR.

Polarogram B was obtained from the buffer solution in which $10^{-4}$ mole/dm$^3$ zinc chloride and 5 mole/dm$^3$ calcium chloride was dissolved, and Polarogram C was recorded from the buffer solution containing 5 mole/dm$^3$ calcium chloride, $10^{-4}$ mole/dm$^3$ zinc chloride and $10^{-4}$ mole/dm$^3$ VCR.

The effect of magnesium ions is shown in FIG. 3, wherein Polarogram A is the same as that of FIG. 2, and Polarograms B and C were recorded for the buffer solutions containing 5 mole/dm$^3$ magnesium chloride instead of calcium chloride and the other constituents were the same as in case of FIG. 2.

Both figures show that increase in the concentration of either the calcium or the magnesium ions results in the development of a polarographic wave characteristic for the free zinc ions. When 5 mole/dm$^3$ calcium or magnesium ion concentration level is reached in all polarograms the same fully developed zinc wave is recorded (which is identical with that of the free zinc ions both in the terms of half-wave potential and limiting (diffusion) current) showing that the zinc ions were set free by the calcium or magnesium ions from the complex. Since an about 50,000-fold amount of calcium or magnesium ions is required for the total substitution of the zinc, the estimated stability of the zinc-VCR complex is 4.5 to 5 order of magnitude higher than those of the complexes formed either with calcium or magnesium.

The stability constant of the complex formed in the reaction of calcium ions with the vincristine ligand was determined by potentiometric equilibrium measurements.

The sulphate of vincristine sulphate parent substance was replaced by chloride ions. Vincristine chloride produced in this way was used for the further equilibrium studies.

Aqueous solutions of pH 5.5 were prepared from the vincristine chloride with VCR concentrations ranging from $5 \times 10^{-4}$ mole/dm$^3$ to $2 \times 10^{-3}$ mole/dm$^3$. The VCR concentration in any individual run of measurements was maintained at a constant level. The ion-strength of the solutions was adjusted to 1.0 by adding sodium nitrate to the solutions to keep the activity coefficients at a constant level.

These VCR solutions were titrated in a computer-controlled potentiometric titration apparatus at 25° C. with 0.1 mole/dm$^3$ calcium chloride standard solutions using a special calcium ion-selective membrane electrode (see DD146,101) and a Ag/AgCl reference electrode (Radelkis 0P0820P model). The concentration of the calcium chloride standard solution was controlled by complexometric titration.

A typical plot of electrode potential values v, calcium ion concentrations is shown in FIG. 4 (pCa= = −log [Ca$^{2+}$], where curve 1 represents the calibration curve of the electrode 2 shows the titration curve obtained for $10^{-3}$ mole/dm$^3$ vincristine solution. The latter proves the complex formation between calcium ions and VCR by showing the decrease in the free calcium ion concentration due to the presence of vincristine.

Based on the potentiometric results, the number of the calcium ions bound by one vincristine molecule ($\bar{n}$) was calculated. The maximum value obtained for $\bar{n}$ was 1 indicating the formation of a complex with a 1:1

Ca:VCR concentration ratio. The stability constant ($\beta$) calculated for this complex from the equilibrium data was found to be log $\beta = 3.27 \pm 0.1$.

FIG. 5 shows the $\bar{n}$ values calculated from the potentiometric data (points) and computed on the basis of the equilibrium constant (continuous line). The good agreement between the experimentally determined and computer-simulated $\bar{n}$ values proves the correctness of the results.

The pH-dependence of the mentioned complex formation reactions was investigated by Calvin type deprotonation equilibrium measurements, by studying the pH-dependence of the polarographic behavior of the Zn-VCR system and by performing the potentiometric calcium ion coordination studies in solutions of different pH. Neither of these investigations has indicated the pH-dependence of the complexation processes in the pH range between 3.5 and 5.5. This proves that the mentioned ions ($Zn^{2+}$, $Ca^{2+}$, $Mg^{2+}$) are coordinated by the oxygen donor atoms of vincristine which are not protonated in the mentioned pH-range.

The metal complexes can be isolated and analysed in solid state.

Stability tests, in which the actual active ingredient content was controlled, were carried out by HPLC method (USP XXI.p. 1118). For instance in the case of VCR the samples were passed through a column (250×4.6 mm.) packed with Nucleosil 5 $C_8$ (Chrompack) at a flow rate of 2 ml./min. Elution was carried out with a mixture of methanol, water and diethylamine (pH 7.5) and the VCR content was determined at 297 nm wavelength with the aid of external standard samples containing vincristine sulphate USP reference standard in aqueous solution.

Accelerated stability tests were conducted from three groups of samples of different origin, namely sample 1 was prepared according to Example 1 of the present application, sample 3 according to Example 1 of Belgian patent No. 897,280 and sample 2 was Oncovin (Eli Lilly) as available on the market. The samples were kept at 75° C. for 5 and 10 days, respectively. The test results are shown in Table 1.

TABLE 1

| No. of sample | VCR content (%) at the start | VCR content (%) at 75° C. after 5 days | VCR content (%) at 75° C. after 10 days | Color** after 5 days | Color** after 10 days |
|---|---|---|---|---|---|
| 1 | 100 | 82.6 | 69.6 | 2y | 3y |
| 2 | 100 | 67.9 | 43.3 | 4y | 5y |
| 3 | 100 | 80.6 | 59.6 | 2y | 4y |

*See: Colorimetric Matching Fluids, VIth Hungarian Pharmacopeia, English Edition, Vol. I, p. 328

From the table it is clear that sample 1, prepared according to the present application (VCR-$Ca^{2+}$ complex), showed much better stability than the other two samples containing the VCR in free form.

For long-term stability tests a solution of a VCR-$Ca^{2+}$ complex prepared according to Example 1, was employed. Into three ampoules 5 ml. of the above solution were filled. The ampoules were sealed under sterile conditions and were kept at 5° C. for 12 months. VCR content determined by HPLC was as shown in Table 2/A. From the results it is clear that practically no decomposition happened.

TABLE 2/A

| | VCR content (%) | | | |
|---|---|---|---|---|
| at start | after 3 months | 6 months | 9 months | 12 months |
| 100.8 | 100.9 | 100.2 | 100.5 | 98.7 |

Essentially following the above method but using vials (normal batch size) the following results were obtained (storage: in refrigerator at 2°–8° C.):

TABLE 2/B

| | at start | after 3 months | 6 months | 9 months | 12 months |
|---|---|---|---|---|---|
| VCR content (%) | 97.5 | 96.9 | 95.4 | 96.3 | 95.1 |
| Related alkaloids (%) | 1.9 | 2.5 | 3.0 | 2.8 | 3.1 |

1-1 ml. portions of a batch of solution prepared according to Example 1 were distributed into 200 vials. The vials were sealed under sterile conditions and 100 of them was stored at 5° C. while the other 100 vials were kept at room temperature for 15 months. Stability data are shown in Table 3.

TABLE 3

| | VCR content (%) stored | |
|---|---|---|
| Storage time | at 5° C. | at room temperature |
| zero time | 100.0 | 100.0 |
| 1 month | 98.0 | 98.4 |
| 2 months | 100.4 | 96.4 |
| 3 months | 100.4 | 98.4 |
| 4 months | 100.4 | 97.6 |
| 5 months | 98.7 | 102.8 |
| 6 months | 99.4 | 100.3 |
| 7 months | 100.3 | 98.3 |
| 8 months | 100.2 | 96.7 |
| 10 months | 99.2 | 94.3 |
| 12 months | 98.3 | 91.7 |
| 15 months | 98.1 | 85.5 |

The data collected in Table 3 show that no decomposition took place at 5° C. and a slight decrease of VCR content could be observed at room temperature.

Experimental data unambiguously confirmed that the complexes formed between a bis-indole compound and a metal ion have excellent stability properties. At 5° C. storage temperature there is no change in the ingredient content even over a 2 years period. In addition, solutions containing said complex can be sterilized at 100° C. without decomposition of the active ingredient.

The invention is elucidated in detail by the aid of the following non-limiting Examples.

EXAMPLE 1

| Vincristine sulphate | 0.1 g |
|---|---|
| propyl p-hydroxybenzoate | 0.02 g |
| acetic acid (98%) | 0.025 g |
| calcium gluconate.$H_2O$ | 0.05 g |
| sodium acetate.$3H_2O$ | 0.06 g |
| methyl p-hydroxybenzoate | 0.13 g |
| ethanol (96%) | 5.0 g |
| mannitol | 10.0 g |
| distilled water for injection | up to 100.0 ml. |

The above quantities of mannitol, calcium gluconate and sodium acetate are dissolved in an aliquot part of distilled water for injection which previously was degassed and flushed with nitrogen. To this solution acetic acid is added. Propyl p-hydroxybenzoate and methyl p-hydroxybenzoate are dissolved in the 96% ethanol and then admixed with the aqueous solution. Finally in a portion of the distilled water the vincristine sulphate is dissolved and added to the other constituents. The volume of the solution is made up to 100 ml. The solution is homogenized, filtered under sterile conditions and distributed into sterile vials under inert protective gas atmosphere and the vials are sealed.

EXAMPLE 2

| Vincristine sulphate | 0.1 g |
|---|---|
| propyl p-hydroxybenzoate | 0.005 g |
| magnesium gluconate | 0.045 g |
| acetic acid (98%) | 0.025 g |
| sodium acetate.3H$_2$O | 0.0256 g |
| methyl p-hydroxybenzoate | 0.05 g |
| mannitol | 5.0 g |
| ethanol (96%) | 5.0 g |
| distilled water for injection | up to 100.0 ml. |

Using the above constituents a similar procedure was followed as in Example 1 to give the aqueous formulation.

EXAMPLE 3

| Vincristine sulphate | 0.1 g |
|---|---|
| acetic acid (98%) | 0.025 g |
| sodium acetate.3H$_2$O | 0.06 g |
| zinc gluconate | 0.049 g |
| benzyl alcohol | 0.9 g |
| ethanol | 5.0 g |
| mannitol | 15.0 g |
| distilled water for injection | up to 100.0 ml. |

In an aliquot part of distilled water which was freshly degassed and flushed with nitrogen the mannitol and zinc gluconate are dissolved. To this solution acetic acid and the mixture of ethanol and benzyl alcohol are added. Finally the vincristine sulphate dissolved in a minimum quantity of the distilled water is added to the solution the volume of which is then made up to 100 ml. The homogenized solution is subjected to sterile filtration, distributed into sterile vials under inert protective gas atmosphere and the vials are sealed.

EXAMPLE 4

| Vincristine sulphate | 0.1 g |
|---|---|
| propyl p-hydroxybenzoate | 0.005 g |
| calcium acetate.H$_2$O | 0.0222 g |
| acetic acid (98%) | 0.025 g |
| sodium acetate.3H$_2$O | 0.0256 g |
| methyl p-hydroxybenzoate | 0.05 g |
| ethanol (96%) | 5.0 g |
| mannitol | 5.0 g |
| distilled water for injection | up to 100.0 ml. |

With the above components a similar procedure was conducted as in Example 1, to give an aqueous formulation.

EXAMPLE 5

| Vincristine sulphate | 0.1 g |
|---|---|
| acetic acid (98%) | 0.025 g |
| sodium acetate.3H$_2$O | 0.026 g |
| calcium gluconate | 0.056 g |
| benzyl alcohol | 0.9 g |
| sorbitol | 5.0 g |
| polyethylene glycol 400 | 10.0 g |
| distilled water for injection | up to 100.0 ml. |

In an aliquot part of freshly degassed and nitrogen-flushed distilled water for injection, sorbitol and calcium gluconate are dissolved in sequence. To this solution acetic acid and the mixture of benzyl alcohol and polyethylene glycol 400 are added. Then vincristine sulphate dissolved in a minimum quantity of distilled water is mixed to the solution which is made up to the final volume, homogenized and filtered under sterile conditions. The sterile solution is distributed into sterile vials under an inert protective gas atmosphere and the vials are sealed.

EXAMPLE 6

| Vinblastine sulphate | 0.1 g |
|---|---|
| propyl p-hydroxybenzoate | 0.005 g |
| calcium acetate.H$_2$O | 0.023 g |
| acetic acid (98%) | 0.049 g |
| sodium acetate.3H$_2$O | 0.049 g |
| methyl p-hydroxybenzoate | 0.05 g |
| ethanol (96%) | 5.0 g |
| mannitol | 5.0 g |
| distilled water for injection | up to 100.0 ml. |

With the above components a similar procedure was conducted as in Example 1, to give an aqueous formulation.

EXAMPLE 7

| Vincristine sulphate | 0.1 g |
|---|---|
| propyl p-hydroxybenzoate | 0.02 g |
| acetic acid (98%) | 0.025 g |
| zinc sulphate | 0.033 g |
| sodium acetate.3H$_2$O | 0.06 g |
| methyl p-hydroxybenzoate | 0.13 g |
| ethanol (96%) | 5.0 g |
| mannitol | 10.0 g |
| distilled water for injection | up to 100.0 ml. |

With the above components a similar procedure was conducted as in Example 1, to give an aqueous formulation.

What we claim is:

1. A complex formed in an aqueous solution at a pH of 3 to 6 between a bivalent metal ion selected from the group consisting of zinc, calcium, magnesium, cobalt, nickel, and iron; and a bis-indole alkaloid of the Formula (I)

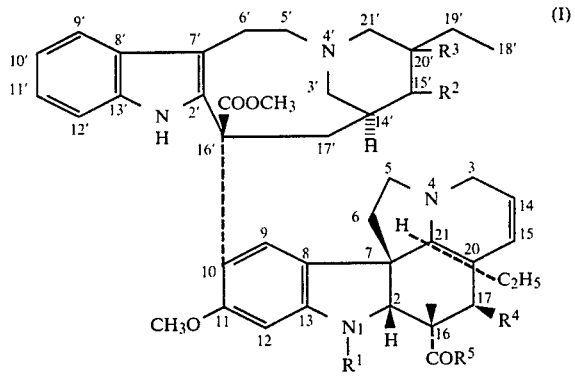

wherein
R$^1$ is methyl,
R$^2$ is hydrogen,
R$^3$ is hydroxy, or
R$^2$ and R$^3$ together form a valence bond,
R$^4$ is hydroxy or acetoxy, and
R$^5$ is methoxy or amino; or
R$^1$ is formyl,
R$^2$ is hydrogen
R$^3$ is hydroxy, or
R$^2$ and R$^3$ together form an expoxy group,
R$^4$ is hydrogen or acetoxy, and
R$^5$ is methoxy; or a pharmaceutically acceptable acid addition salt thereof; wherein the molar ratio of the bis-indole alkaloid to the bivalent metal ion is at least 1:1.

2. The complex defined in claim 1 wherein the bivalent metal ion is selected from the group consisting of zinc, calcium and magnesium.

3. The complex defined in claim 1 wherein the molar ratio of the bis-indole alkaloid to the bivalent metal ion is 1:1.

4. The complex defined in claim 1 which is the vinblastine complex of zinc, magnesium or calcium.

5. The complex defined in claim 1 which is the vincristine complex of zinc, magnesium or calcium.

6. The complex defined in claim 1 which is buffered at a pH of 3 to 6.

7. A stable, injectable, antineoplastic pharmaceutical composition which comprises:
(a) a pharmaceutically effective amount of a complex formed in aqueous solution at a pH of 3 to 6 between a bivalent metal ion selected from the group consisting of zinc, calcium, magnesium, cobalt, nickel and iron; and a bis-indole alkaloid of the Formula (I)

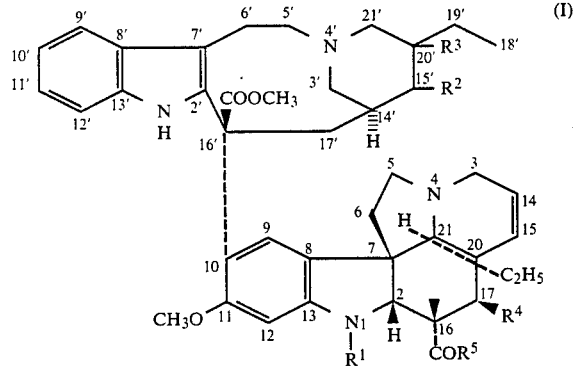

wherein
R$^1$ is methyl,
R$^2$ is hydrogen,
R$^3$ is hydroxy, or
R$^2$ and R$^3$ together form a valence bond,
R$^4$ is hydroxy or acetoxy, and
R$^5$ is methoxy or amino; or
R$^1$ is formyl,
R$^2$ is hydrogen,
R$^3$ is hydroxy, or
R$^2$ and R$^3$ together form an epoxy group.
R$^4$ is hydrogen or acetoxy, and
R$^5$ is methoxy; or a pharmaceutically acceptable acid addition salt thereof; wherein the molar ratio of the bis-indole alkaloid to the bivalent metal ion is at least 1:1;
(b) a buffer capable of maintaining the pH of the pharmaceutical composition between 3 and 6; and
(c) a pharmaceutically acceptable inert carrier suitable for an injectable composition.

8. An antineoplastic method of treatment which comprises the step of intravenously administering to a patient in need of said treatment, a therapeutically effective amount of the stable, injectable antineoplastic pharmaceutical composition defined in claim 7.

9. A process for preparing a complex formed in aqueous solution at a pH of 3 to 6 between a bivalent metal ion selected from the group consisting of zinc, calcium, magnesium, cobalt, nickel, and iron; and a bis-indole alkaloid of the Formula (I)

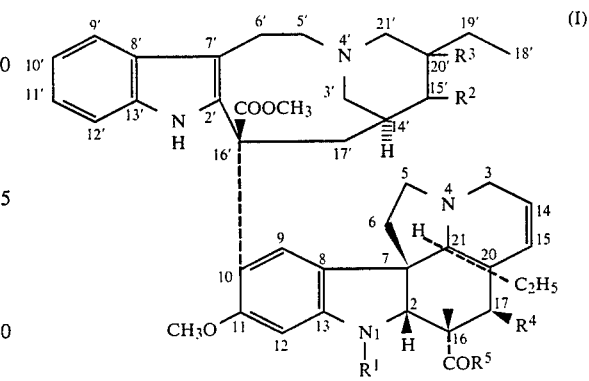

wherein
R$^1$ is methyl,
R$^2$ is hydrogen,
R$^3$ is hydroxy, or
R$^2$ and R$^3$ together form a valence bond,
R$^4$ is hydroxy or acetoxy, and
R$^5$ is methoxy or amino; or
R$^1$ is formyl,
R$^2$ is hydrogen,
R$^3$ is hydroxy, or
R$^2$ and R$^3$ together form an epoxy group.
R$^4$ is hydrogen or acetoxy, and
R$^5$ is methoxy; or a pharmaceutically acceptable acid addition salt thereof; wherein the molar ratio of the bis-indole alkaloid to the bivalent metal ion is at least 1:1, which comprises the step of:
reacting the compound of the Formula (I) or a pharmaceutically acceptable acid addition salt thereof with a water-soluble salt of the bivalent metal ion, in aqueous solution, at a buffered pH of 3 to 6 in which the amounts of the compound of the Formula (I) or the pharmaceutically acceptable acid addition salt thereof and the water-soluble salt of the bivalent metal ion produce a complex having a molar ratio of the compound or salt to the metal ion of at least 1:1.

* * * * *